United States Patent [19]

Liebermann et al.

[11] Patent Number: 5,498,873
[45] Date of Patent: Mar. 12, 1996

[54] REFRIGERANT IMPURITY ANALYZER

[75] Inventors: Leonard Liebermann, La Jolla; Philip Salzmann, Cardiff, both of Calif.

[73] Assignee: TIF Instruments, Inc., Miami, Fla.

[21] Appl. No.: 340,266

[22] Filed: Nov. 15, 1994

[51] Int. Cl.$^6$ .................. G01J 5/44; G01J 5/46; G01N 21/61
[52] U.S. Cl. ................ 250/343; 250/345; 250/351
[58] Field of Search ................ 250/343, 345, 250/351

[56] References Cited

U.S. PATENT DOCUMENTS

| | | | |
|---|---|---|---|
| 3,820,901 | 6/1974 | Kreuzer | 250/345 |
| 3,861,809 | 1/1975 | Hall, Jr. | 250/343 |
| 3,911,277 | 10/1975 | Cederstrand et al. | 250/343 |
| 3,968,370 | 7/1976 | Luft | 250/343 |
| 4,193,695 | 3/1980 | Kojima et al. | 250/343 |
| 4,236,827 | 12/1980 | Horiba et al. | 250/351 |
| 4,255,971 | 3/1981 | Rosencwaig | 73/606 |
| 4,350,447 | 9/1982 | Landa | 400/118 |
| 4,437,005 | 3/1984 | Ophoff et al. | 250/343 |
| 4,682,031 | 7/1987 | Fabinski et al. | 250/345 |
| 4,866,681 | 9/1989 | Fertig | 250/345 |
| 4,906,796 | 3/1995 | Yates | 570/179 |
| 5,020,977 | 6/1991 | Lucas | 417/322 |

OTHER PUBLICATIONS

Goldan, Paul D., An acoustically resonant system for detection of low level infrared absorption in atmospheric pollutants, Oct. 1974, p. 4350, FIG. 1.

*Primary Examiner*—Constantine Hannaher
*Assistant Examiner*—Virgil O. Tyler

[57] ABSTRACT

A portable refrigeration gas analyzer employs infrared spectroscopy to detect adulterant refrigerant gases in existing R12 refrigeration systems. The analyzer can detect contaminants such as R134a, R22, and butane in concentration as low as 1% by volume. A rugged opto-acoustical infrared narrow band sensor is suitable for field use in the repair of refrigeration systems.

4 Claims, 1 Drawing Sheet

REFRIGERANT IMPURITY ANALYZER

FIELD OF THE INVENTION

This device relates to infrared spectroscopic analysis of gaseous impurities in refrigerant gas, specifically to check for undesirable impurities or adulterants in existing refrigeration systems.

DESCRIPTION OF PRIOR ART

Refrigerant gases containing chlorine, for example difluorodichloromethane (known as "R12"), are rapidly being phased out as harmful to the environment. Although the majority of refrigeration systems presently employ R12, production of this chemical has been greatly curtailed and will soon cease. It is now required in the U.S. that the R12 gas in systems needing repair or replacement be recovered (and reclaimed) for further use.

Because of the growing shortage of R12 and restrictions on its sale, some refrigeration systems based on R12 have been adulterated with other more available refrigerants. For example, the refrigerant tetrafluoroethane (known as "134a"), is now readily available in auto supply stores. Another refrigerant, butane, is also used as an adulterant although it can be explosive. Although adulteration may eventually lead to failure of the system the practice is widespread, deliberately or out of ignorance.

Refrigeration systems needing repair should have the refrigerant checked for adulteration for two reasons: First, if the refrigerant is to be emptied (and reclaimed), its purity should be checked lest it contaminate the reclamation equipment and its reservoir. Secondly, more extensive repairs may be necessary if the refrigeration system is known to have been adulterated with an improper refrigerant.

The use of spectrum analysis for checking gaseous purity is well-known. The infrared absorption spectrum contains characteristic information on the molecular composition of each gas and is capable of detecting impurities with high precision. Infrared instruments are available commercially for this purpose employing either dispersive (grating, or prism) or non-dispersive (spectrum line filter) technology. These instruments are complex, laboratory-type instruments, not intended for portability.

The non-dispersive instruments employ narrow band filtering to detect the infrared absorption spectrum. Commonly, they employ the opto-acoustical method to obtain narrow band filtering. However the condenser microphone hitherto used in these instruments is sensitive to external sounds which interfere; these instruments require very quiet surroundings. Furthermore these non-dispersive instruments only check for an individual specified gas and ignore any other impurities. These properties render previous opto-acoustical infrared analyzers totally impractical for field use in connection with air conditioning and refrigeration repairs. Although there is a current need, refrigeration purity analyzers are rarely if ever found in repair shops. Consequently the limited reservoir of recovered R12 will gradually become contaminated unless purity analyzers become routinely used in refrigeration repair.

OBJECTS AND ADVANTAGES

A general object is provide a non-dispersive infrared absorption spectrum analyzer for detecting impurities in R12 refrigerant gas.

Another general object is to provide an R12 refrigerant purity analyzer which is simple to use and suitable for field analysis during repair of installed refrigeration systems.

Still one more general object is to construct a narrow-band infrared sensor suitable for detecting changes in the infrared absorption spectrum of refrigerant R12 caused by gaseous impurities.

A specific object is to provide a non-dispersive spectrum analyzer which utilizes a narrow band opto-acoustic filter in the infrared region to detect changes in light absorption as a measure of impurity concentration.

Another specific object is to construct a narrow band infrared sensor which can withstand rugged use in the field and will be unresponsive to external sound and vibration.

Another more specific object is to provide an instrument which can detect any of the following contaminants in refrigerant R12 such as R134a, R22 (monochlorodifluoromethane), butane and propane in concentration as low as 1% by volume.

In accordance with the principles of the invention, this R12 purity analyzer consists of the following elements in an integral combination: A source of infrared radiation whose emission spectrum embraces a fundamental absorption band of the gaseous impurities to be detected; a tubular sample cell through which the radiation passes, containing the refrigerant R12 whose purity is to be analyzed; an infrared detector in the form of a narrow band sensor which transforms the detected radiation into an electrical signal. Further in accordance with this invention the narrow reception band of the sensor is centered on a spectral absorption region of the gaseous impurity to be detected.

The sensor is based on the conventional opto-acoustic principle which functions in the following manner: The infrared radiation enters a sealed chamber through a transparent window. The chamber contains gas which absorbs the radiation and is thereby heated. The heated gas results in a pressure rise in the chamber which is detected by a microphone. Importantly, the gas absorbs radiation only within its own characteristic spectrum, leading to a narrow band filter determined by the chamber gas.

In accordance with this invention the sensor chamber is filled with 134a at atmospheric pressure. If the sample tube which is transmitting radiation from source to sensor also contains traces of 134a, the sensor will detect increased absorption of radiation in the tube, compared to pure R12. However it has been unexpectedly found that this sensor is also responsive to the following impurities which are often deliberately added to R12 to replace any losses: Butane, propane, and R22. The explanation for this favorable result must reside in the narrow band filter characteristics of this sensor which appear to overlap absorption line spectra of these impurities.

These and other objects, advantages, and features of the present invention will be more fully understood and appreciated upon consideration of the following detailed description of a preferred embodiment, presented in conjunction with accompanying drawings.

DETAILED DESCRIPTION OF A PREFERRED EMBODIMENT

Figure 1:
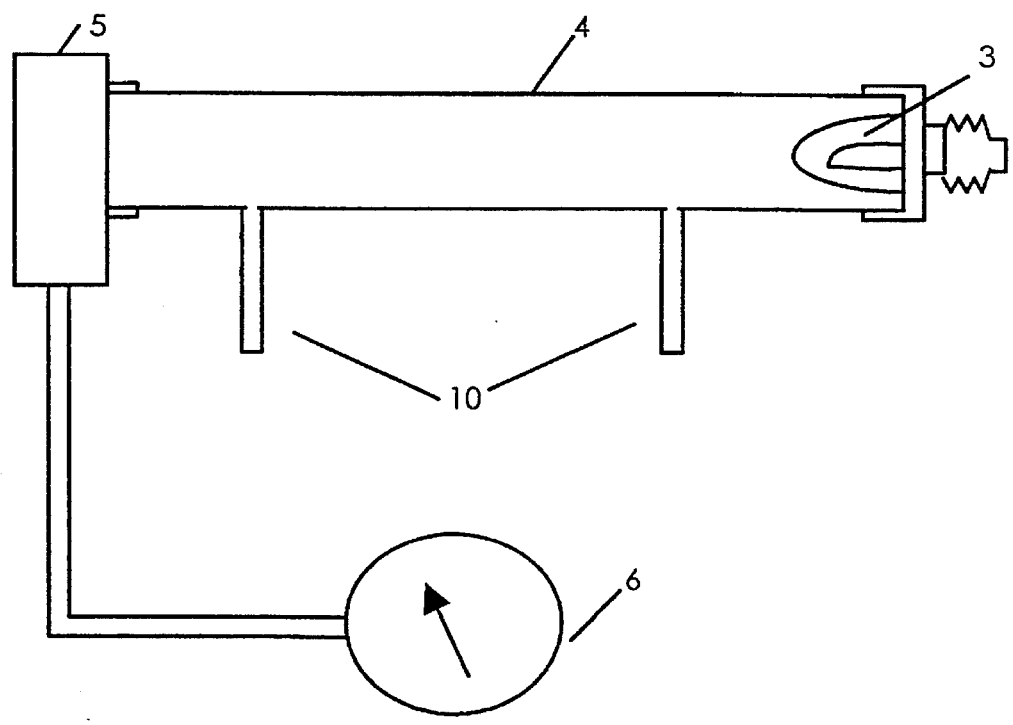
FIG. 1 shows a schematic arrangement of the various optical components for measuring the infrared absorption.

An overall schematic of a preferred embodiment of the present invention is shown in FIG. 1. The four basic elements required by this invention to measure the infrared absorption of refrigerant R12 are shown. According to the figure the infrared source 3 is arranged to transmit radiation into the cylindrical sample container 4. The transmitted radiation passes through the sample tube and is detected by the sensor 5, which contains the narrow band optical filter in an integral combination. The ends of the cylindrical sample tube 4 are blocked by the source 3 and sensor 5 to form a substantially closed container for the gaseous sample. The electrical signal from the sensor, indicative of absorption in the sample, is displayed on meter means 6 to provide a quantitative measure of the amount of impurity gas present in the refrigerant R12 sample.

Figure 2:
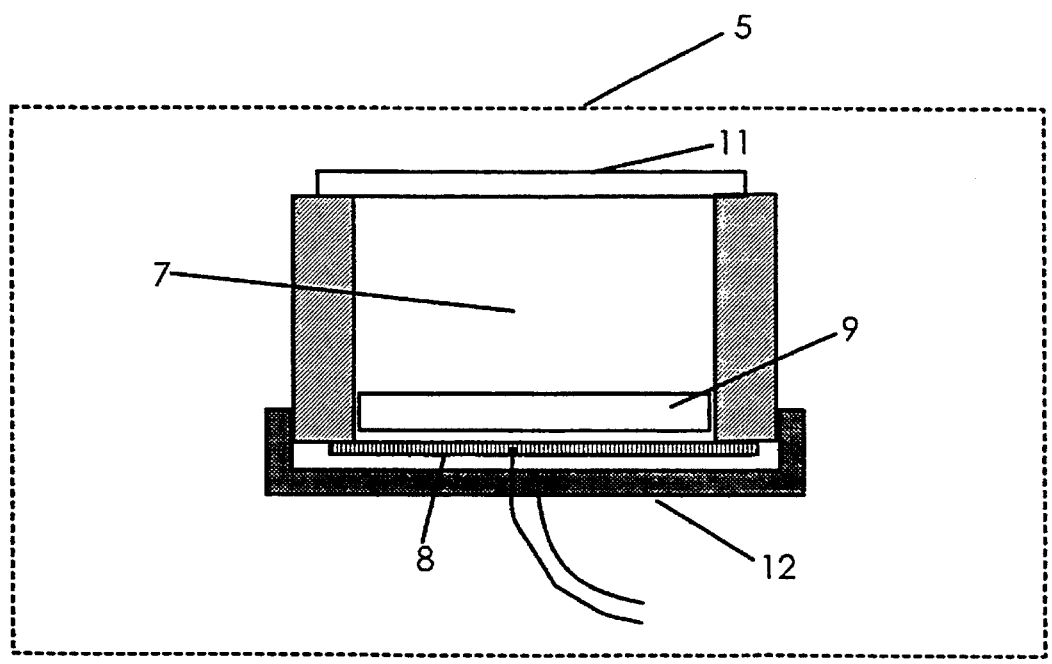
FIG. 2 shows the construction details of the narrow band infrared opto-acoustic sensor.

The details of the construction of sensor 5 are shown in FIG. 2. The absorption chamber 7 containing 134a gas, is of cylindrical form approximately ½ inch in diameter and ½ inch in height. The chamber is sealed at one end by a glass window 11; the glass is preferably of the type known as "extra white, low iron" which provides adequate transmission of the infrared band utilized here. The opposite end of the cylindrical cavity is sealed by a ceramic piezoelectric disk 8. The latter is readily available commercially as a resonant sound source for producing a tone at 3 to 4 kilohertz. The interior of the chamber is polished to avoid absorption at the walls. In addition a loosely fitted polished metallic disk 9 is installed in front of (but not in contact with) the piezo element to provide reflection and inhibit heating by the infrared light. The back side of the piezo is enclosed in an air-tight cover 12 to avoid the effect of rapid atmospheric pressure changes on the piezo element. The sealed absorption chamber is filled with 134a refrigerant at atmospheric pressure.

The sample container 4 is constructed from standard ½ copper pipe of length 9 inches and inside diameter ½ inch. The interior of the pipe is highly polished to yield good radiation transmission. Typically, inlet and outlet ports 10 are provided to allow circulation of the sample gas.

The source of infrared radiation 3 is a standard 7 volt bayonet-type lamp bulb. The lamp is operated at reduced voltage usually about 3–5 volts. The lamp is continually flashed on and off with a period of 1 second. This flashing source provides a periodic pressure change on the piezo element 8 and consequently a substantially sine-wave electrical signal output.

The sensor, sample pipe, and lamp bulb are joined together mechanically to form an integral tubular unit which is both compact and rugged to withstand field usage in conjunction with repair of installed systems. The tubular unit together with the electrical signal meter circuitry is mounted into a small carrying case for portability.

Although the above description above contains many specificity's, these should not be construed as limiting the scope of the invention but merely as providing illustrations of some preferred embodiments. The scope of the invention should be determined by the following claims rather than by these examples.

We claim:

1. A non-dispersive spectroscopic gaseous impurity analyzer including a flashing incandescent lamp light source and a narrow band infrared absorption sensor comprising:

(a) a chamber sealed at one end by a window which is substantially transparent to infrared light, and (b) a ceramic piezoelectric disk sealing the other end of said chamber, and (c) a reflecting disk located in front of, but not contacting said piezoelectric disk, and (d) a hollow shield covering the external face of said piezoelectric disk whereby atmospheric pressure changes are excluded from acting on said piezoelectric disk.

2. A impurity analyzer for gaseous refrigerant R12 including a flashing incandescent lamp bulb light source, a tube containing a sample of said refrigerant gas through which said light traverses, and a narrow band infrared sensor for detecting said traversed light comprising:

(a) a gas filled absorption chamber sealed at one end by a window which is transparent to said light, and (b) a ceramic piezoelectric disk sealing the other end of said chamber, and (c) a reflecting disk located in front of, but not contacting said piezoelectric disk, and (d) a hollow shield covering the external face of said piezoelectric disk whereby atmospheric pressure changes are excluded from acting on said piezoelectric disk.

3. The impurity analyzer according to claim 2, wherein said gaseous impurity analyzer for refrigerant R12 includes portable means for field analysis of refrigerant in installed refrigeration systems.

4. The impurity analyzer according to claim 2, in which said gas sealed in said absorption chamber is substantially pure refrigerant 134a.

\* \* \* \* \*